(12) United States Patent
Ramey et al.

(10) Patent No.: US 7,163,912 B2
(45) Date of Patent: *Jan. 16, 2007

(54) LUBRICANT COMPOSITIONS CONTAINING AN OVERBASED AMORPHOUS ALKALINE EARTH METAL SALT AS A METAL PROTECTANT

(75) Inventors: Chester E. Ramey, Chagrin Falls, OH (US); James E. Reddy, Lyndhurst, OH (US)

(73) Assignee: OMG Americas, Inc., Westlake, OH (US)

( * ) Notice: Subject to any disclaimer, the term of this patent is extended or adjusted under 35 U.S.C. 154(b) by 469 days.

This patent is subject to a terminal disclaimer.

(21) Appl. No.: 10/664,433

(22) Filed: Sep. 19, 2003

(65) Prior Publication Data

US 2004/0063589 A1    Apr. 1, 2004

Related U.S. Application Data

(63) Continuation-in-part of application No. 10/643,137, filed on Aug. 18, 2003, now Pat. No. 6,844,386, which is a continuation-in-part of application No. 10/379,048, filed on Mar. 3, 2003, now Pat. No. 6,639,090, which is a continuation-in-part of application No. 09/861,393, filed on May 18, 2001, now Pat. No. 6,689,893.

(51) Int. Cl.
*C10M 159/20*    (2006.01)
*C07C 51/00*    (2006.01)

(52) U.S. Cl. .................. 508/460; 554/156; 554/157

(58) Field of Classification Search ................ 508/460
See application file for complete search history.

(56) References Cited

U.S. PATENT DOCUMENTS

| | | | |
|---|---|---|---|
| 2,616,904 A | 11/1952 | Asseff et al. ................ 260/399 |
| 2,760,970 A | 8/1956 | Le Suer ....................... 260/429 |
| 2,767,164 A | 10/1956 | Asseff et al. ................ 260/139 |
| 2,798,852 A | 7/1957 | Wiese et al. ................ 252/42.7 |
| 2,802,816 A | 8/1957 | Asseff et al. ................ 260/139 |
| 2,971,014 A | 2/1961 | Mastin ........................ 260/398 |
| 2,989,463 A | 6/1961 | Mastin ......................... 252/25 |
| 3,027,325 A | 3/1962 | McMillien et al. ........... 252/33 |
| 3,031,284 A | 4/1962 | Andress, Jr. et al. ........... 44/76 |
| 3,147,232 A | 9/1964 | Norman et al. ............... 260/23 |
| 3,194,823 A | 7/1965 | Le Suer et al. ............. 260/414 |
| 3,342,733 A | 9/1967 | Robbins et al. ................ 252/33 |
| 3,533,975 A | 10/1970 | Scullin ......................... 260/23 |
| 3,766,066 A | 10/1973 | McMillen ................... 252/32.7 |
| 3,766,067 A | 10/1973 | McMillen ..................... 252/33 |
| 3,773,664 A | 11/1973 | Lesuer ....................... 252/40.7 |
| 3,779,922 A | 12/1973 | LeSuer ...................... 252/34.7 |
| 4,159,973 A | 7/1979 | Hoch et al. ............. 260/23 XA |
| 4,252,698 A | 2/1981 | Ito et al. .................. 260/18 EP |
| 4,501,840 A | 2/1985 | Werle et al. ................. 524/387 |
| 4,661,544 A | 4/1987 | Quinn ......................... 524/109 |
| 4,665,117 A | 5/1987 | Quinn ......................... 524/327 |
| 4,743,397 A | 5/1988 | Quinn .................... 252/400.61 |
| 5,147,917 A | 9/1992 | Sugawara et al. .......... 524/257 |
| 5,259,966 A | 11/1993 | Burke, Jr. et al. ............ 252/18 |
| 5,322,872 A | 6/1994 | Quinn ......................... 524/186 |
| 5,501,807 A | 3/1996 | Benda et al. .................. 252/18 |
| 5,519,076 A | 5/1996 | Odaira et al. ................ 524/112 |
| 5,534,169 A | 7/1996 | Vinci ......................... 508/460 |
| 5,746,961 A | 5/1998 | Stevenson et al. .......... 264/255 |
| 5,830,832 A | 11/1998 | Benda et al. ................ 508/460 |
| 5,830,935 A | 11/1998 | Khattar et al. .............. 524/114 |
| 5,859,267 A | 1/1999 | Khattar et al. .................. 554/4 |
| 5,919,741 A * | 7/1999 | Jaynes et al. ................ 508/460 |
| 6,262,161 B1 | 7/2001 | Betso et al. ................. 524/425 |
| 6,348,164 B1 * | 2/2002 | Khattar et al. .............. 252/404 |
| 6,569,821 B1 | 5/2003 | Ibrahim et al. ............. 508/396 |
| 6,596,672 B1 * | 7/2003 | Carrick et al. .............. 508/192 |
| 6,639,090 B1 * | 10/2003 | Ramey et al. .............. 554/156 |
| 6,689,893 B1 * | 2/2004 | Reddy et al. ............... 554/156 |
| 6,773,631 B1 * | 8/2004 | Reddy et al. .......... 252/400.52 |
| 6,844,386 B1 * | 1/2005 | Reddy et al. ............... 524/400 |

FOREIGN PATENT DOCUMENTS

| | | |
|---|---|---|
| DE | 198 60 798 A1 | 7/2000 |
| EP | 0 398 505 A1 | 11/1990 |
| EP | 0 421 933 A1 | 4/1991 |
| RU | 2 087 491 C1 | 8/1997 |
| WO | WO 89/09811 | 10/1989 |
| WO | WO 94/21587 | 9/1994 |
| WO | WO 99/10307 | 3/1999 |
| WO | WO 01/12708 A1 | 2/2001 |
| WO | WO 02/094925 A2 | 11/2002 |

* cited by examiner

*Primary Examiner*—Ellen M. McAvoy
(74) *Attorney, Agent, or Firm*—Wood, Herron & Evans, L.L.P.

(57) ABSTRACT

Lubricant compositions are made containing, as a metal protectant additive, an overbased amorphous alkaline earth metal salt of fatty acid. The additive is added in either a liquid or powdered form to the base oil in the composition. The overbased additive in the lubricating composition serves as a metal protectant to provide detergency, friction-modifying and acid-neutralizing properties to the compositions.

59 Claims, No Drawings

LUBRICANT COMPOSITIONS CONTAINING AN OVERBASED AMORPHOUS ALKALINE EARTH METAL SALT AS A METAL PROTECTANT

RELATED APPLICATIONS

This application is a continuation-in-part of U.S. patent application Ser. No. 09/861,393, filed on May 18, 2001, Ser. No. 10/379,048, filed on Mar. 3, 2003, now U.S. Pat. Nos. 6,689,893 and 6,639,090, and Ser. No. 10/643,137, filed on Aug. 18, 2003 now U.S. Pat. No. 6,844,386, The entire disclosures of these applications are incorporated herein by reference.

FIELD OF THE INVENTION

The present invention relates to lubricant compositions containing, as a metal protectant additive, overbased amorphous alkaline earth metal salts of fatty acids. The overbased additive in the lubricating composition serves as a metal protectant to provide detergency, friction-modifying and acid-neutralizing properties to the composition.

BACKGROUND OF THE INVENTION

The preparation of overbased calcium or barium salts of carboxylic acids, alkyl phenols, and sulfonic acids are disclosed in the following U.S. Pat. Nos. 2,616,904; 2,760,970; 2,767,164; 2,798,852; 2,802,816; 3,027,325; 3,031,284; 3,342,733; 3,533,975; 3,773,664; and 3,779,922. The use of these overbased metal salts in the halogen-containing organic polymer is described in the following U.S. Pat. Nos. 4,159,973; 4,252,698; and 3,194,823. According to the teachings of U.S. Pat. No. 4,665,117, light colored alkali or alkaline earth metal salts are prepared where alkyl phenol is used as a promoter.

With the movement to replace heavy metals in various compositions, liquid calcium products have been developed. Low metal concentrations, poor compatibility and haziness in clear products have severely limited the universal acceptance of calcium based liquid compositions. Problems are encountered in the stability of these compositions upon standing or storage. Storage stability is due to the incompatibility among the metal salts employed in the composition and is exhibited by increased turbidity, viscosity, or insoluble solids over time.

As a result, the liquid calcium compositions are no longer homogeneous or readily pourable and must be specially treated in order to be used. U.S. Pat. No. 5,322,872 is directed to stabilized compositions of mixed metal carboxylates having improved storage stability. According to this patent, a complexing agent is added to the mixed metal carboxylate in order to improve shelf stability. Complexing agents disclosed in this patent include phosphines, phosphites aromatic cyanides, aromatic hydroxy compounds, oximes and other compounds. U.S. Pat. Nos. 5,830,935 and 5,859,267 have also issued as directed to processes for improving the basic metal composition.

U.S. Pat. Nos. 3,766,066 ('066) and 3,766,067 ('067) disclose the preparation of solid calcium-containing micellar complexes from homogenized carbonated calcium overbased organic acid salts with the aid of "conversion agents" such as water and alcohols. The '067 patent teaches that to prepare the desired micellar complexes from the overbased salts it is first necessary to subject a solution of those salts in inert organic liquid diluents to a homogenization step with vigorous agitation in the presence of water, alcohols or mixtures of alcohols and water. The homogenization is accompanied by a "thickening" or "gelling" phenomenon to produce crystalline particles characterized by an x-ray diffraction pattern corresponding to that of calcite. However, x-ray diffraction studies of the starting salt solutions do not indicate the presence of any crystalline calcium carbonate. In fact, the '066 patent teaches that the calcium carbonate present in the starting non-homogenized solution appears to be amorphous. The amorphous metal salts or complexes present in the material are unquestionably transformed to crystalline particles on homogenization according to the '066 and '067 patents. U.S. Pat. No. 5,534,169 also teaches the conversion of a Newtonian overbased calcium carboxylate to a non-Newtonian dispersion of calcite particles in order to produce a material useful for reducing friction. U.S. Pat. No. 5,830,832 also discloses the preparation of powdered calcium overbased soaps from branched oxo-acids.

Overbased metal components have been used in lubricant compositions. For example, overbased metal sulfonates have normally been used as detergents. Notwithstanding the state of the art as exemplified by the above patents and the current state of the art, there is a need for further improvements in the use of overbased alkaline earth metal salts in lubricating oil compositions.

SUMMARY

The present invention relates to lubricating oil compositions containing a metal protectant additive which is an overbased amorphous alkaline earth metal salt of a fatty acid. The overbased amorphous metal salt is used as an additive in a haze free liquid form or powdered form. Each of these forms results from a particular method of making as described in our earlier applications Ser. Nos. 09/861,393 and 10/379,048 referred to above and incorporated herein by reference. Haze free overbased liquid additives are made by that method and the powdered additive is made from the overbased liquid.

The lubricating compositions contain the metal protectant additive in an effective amount to protect the metal during lubrication. It has been found that the overbased metal additive provides a trilogy of properties in the lubricant composition including detergency, friction-modifying and acid-neutralizing properties. The benefits of the invention are obtained when the additive is contained in the lubricant composition in an effective amount of about 0.5 to about 7% by weight, even up to 15% by weight, of the active overbased metal salt based upon the total weight of the composition. It has also been found that the overbased additives of this invention provide significant improvements over overbased metal sulfonates which heretofore have been used as a standard additive in lubricant compositions. For example, unlike these other overbased metal additives which have been used in lubricants, the additives of this invention provide significant benefits in the neutralization of adverse acidic moieties in the composition, along with improved detergency and anti-wear properties.

When the overbased metal liquids are used as an additive, they are contained in the liquid hydrocarbon which has been employed to produce them according to the process of the invention. In this liquid form, the additive is contained in a haze free liquid stable state for addition to the lubricating oil. When the powder form of the additive has been isolated, it may be added directly to the lubricating oil composition. In both forms, a level of about 0.5 to about 7% by weight of the basic metal salt in the lubricating oil is preferred. Higher levels of the additive may be employed in the lubricating oil up to about 15% by weight, however, at higher levels there may not be a particular advantage in achieving the properties of detergency, acid-neutralization and anti-wear, depending upon the end use of the lubricating composition.

In contrast to other overbased lubricant additives which may include needles or platelets which adversely increase the viscosities or rheologies in the lubricating oils, the overbased metal additives of this invention offer the improved properties without adversely affecting viscosities and end uses.

The above advantages, benefits and further understanding of this invention will be apparent with reference to the following detailed description and preferred embodiments.

DETAILED DESCRIPTION AND PREFERRED EMBODIMENTS

The liquid or powder additives of this invention comprise particles of an amorphous alkaline earth metal carbonate complexed with an amorphous alkaline earth metal carboxylate of a fatty acid. These powders or liquids are referred to sometimes hereinafter more simply as "powdered or liquid overbased amorphous alkaline earth metal salt(s)" or "powdered or liquid overbased amorphous alkaline earth metal carboxylate(s)/carbonate(s)". Overbased amorphous calcium and barium salts are preferably provided and, in a preferred form of the invention, the additives are essentially free of a phenol or a phenolic derivative. The powdered amorphous overbased salts are essentially solid particles which are agglomerated micelles of the amorphous metal salt, like the metal carbonate, complexed with the amorphous metal carboxylate. The agglomerated particles generally range from about 50 microns in size.

The process for preparing the liquid or powdered overbased amorphous alkaline earth metal salts involves reacting an alkaline earth metal base and a fatty acid with an equivalent ratio of metal base to fatty acid being greater than 1:1 in the presence of a liquid hydrocarbon. A surfactant and catalyst are used to promote the reaction. The mixture is acidified, preferably by carbonation, to produce an amorphous alkaline earth metal carbonate. In a preferred method, during carbonation, a dispersion of alkaline earth metal base, a liquid hydrocarbon, and an aliphatic alcohol having at least 8 carbon atoms, is added in relative amounts to produce a stable haze free liquid reaction product. Water is removed from the reaction product to obtain a shelf stable haze free liquid overbased alkaline earth metal salt. The powdered overbased amorphous salt is then isolated by adding a sufficient amount of solvent for the liquid hydrocarbon/alcohol of the haze free liquid to cause particles of the overbased amorphous salt to agglomerate and separate. The agglomerated particles are then isolated by filtration and drying to a state that particles are handleable as a solid powder.

As reported in our earlier application Ser. No. 09/861,393, filed on May 18, 2001, it has been found important during carbonation to add the dispersion of metal base, liquid hydrocarbon and aliphatic alcohol in relative amounts at a controlled rate to produce the stable haze free liquid reaction product. There are a number of reasons which are believed to contribute to the formation of a stable haze free liquid which is then filterable to remove impurities and byproducts of the reaction. Up to the discoveries made in accordance with the principles of this invention, it was not considered possible to make in a practical or commercial operation an overbased calcium fatty acid salt, for example, that may be filtered at commercial or practical rates to remove unwanted impurities and byproducts of the reaction to produce a shelf stable haze free liquid. In contrast, it has been found that by the continuous addition of the dispersion or slurry of base during carbonation, such results are achievable. It is believed that the metal base slurry prevents the formation of undesirable calcium carbonate crystals or byproducts in the desired overbased metal salt. These undesirable moieties prevent the formation of stable haze free products which are filterable. In other words, the metal base slurry is added at a controlled rate which does not exceed the rate of the desired product-forming reaction. The reaction is controlled by continuous or incremental addition of the metal base to make the calcium ions immediately available for the desired reaction as opposed to allowing the metal base, for example lime, to react and form a byproduct. Excessive byproduct or lime coated with calcium carbonate is believed to render the liquid product unfilterable. Using this procedure, the pH is controlled during the reaction so that the fatty acid is neutralized and the pH rises to about 10–12 with the continued addition of base to produce dissolved metal ion which reacts with $CO_2$ during carbonation to produce the desired product. It is believed if the reaction rate is not controlled, and the base is not dissolved, then solid base reacts or is coated with calcium carbonate to form undesirable byproducts. The formation of undesirable byproducts of the reaction renders the final product unstable and unfilterable. It has been found that powdered overbased amorphous salts may be produced from the haze free liquids of the overbased alkaline earth metal fatty acid salts.

A number of benefits are obtained by the liquid or powdered additives and processes of this invention. The liquids and powders provide shelf stable overbased alkaline earth metal fatty acid salts. In particular, shelf stabilities are achieved with the liquids and powders being free of phenol and phenolic derivatives such as phenolic reaction products. This is an especially desirable advantage in view of the efforts of the trade to reduce or eliminate such phenolic products because of environmental concerns. Also, as developed above, such phenols are a source of color development. In particular, presently available liquid overbased calcium fatty acid carboxylates exhibit the development of turbidity or haze, whereas the liquid or powdered additives of this invention remain stable over extended periods of time. The liquids and isolated powders of this invention also allow easy handling and storage. The powders may be dispersed in the oils or liquid hydrocarbons and other solvents to form haze free liquids. Thus, the redispersion of the powders is not restricted to certain media. The promoters and reaction diluents are removed from the powders. Also, higher concentrations of up to about 25% of calcium, for example, are achievable upon redispersion.

A. Liquid or Powdered Additives of Overbased Amorphous Alkaline Earth Metal Salts In one preferred form of the invention, the powdered or liquid overbased amorphous salts are derived from a shelf stable haze free liquid of an amorphous overbased alkaline earth metal salt of a fatty acid which comprises an alkaline earth metal carbonate, an alkaline earth metal carboxylate of a fatty acid, a liquid hydrocarbon, and an aliphatic alcohol having at least 8 carbon atoms, with the liquid being preferably free of a phenol or a phenolic derivative such as a phenolic reaction product.

The powdered overbased amorphous salt is isolated by precipitation from the liquid overbased salts using a solvent or liquid precipitating agent, such as isopropyl alcohol, for the liquid hydrocarbon and/or alcohols and glycols which may be present, to cause solid particles of the overbased salts to form by agglomeration of the amorphous particles. The agglomerated particles of the overbased salts are then obtained by filtration and drying. It is preferred to precipitate the solids from the liquid salts to eliminate the need to distill volatiles or use specialized equipment to particulate and collect the powder, for example, by spraying. The agglomerated particle sizes for the overbased amorphous salts range from about 50 microns, although particle size is not considered critical. It has also been found that these powders are dispersible in liquid hydrocarbons and other solvents to prepare haze free liquids which have a wide variety of end uses, as reported hereinafter.

Other solvents, or liquid precipitating agents, such as methanol, ethanol, propanol, butanol, and glycol ethers may be used to precipitate the powders or agglomerated particles from the liquid overbased salts. The lower alcohols are preferred because they are more readily removed from the filtered product by drying. Such solvents or liquids have been used as "conversion agents" to convert the Newtonian overbased liquids to non-Newtonian colloidal systems with the separation of crystalline calcite particles as disclosed in U.S. Pat. Nos. 3,766,066 and 3,766,067, as stated in the above background of this invention. In contrast, according to this invention, the overbased amorphous salts have been isolated by the addition of an excessive amount of the solvent for the liquid hydrocarbon and alcohol phase of the haze free overbased liquids. It has been found, by so treating the haze free overbased liquids of this invention, that powdered overbased amorphous salts can be isolated in contrast to the crystalline calcite-containing powders of the mentioned prior patents. Thus, when the solvents are added in sufficient amounts of about 5 to 1 of the haze free overbased liquids, the overbased amorphous salts agglomerate to produce the powdered overbased amorphous products of this invention. The process is believed to be solvent extraction of the liquid hydrocarbons from the liquid overbased compositions.

The fatty acid of the overbased liquid carboxylate is generally a $C_{12}$–$C_{22}$ fatty acid, including, for example, lauric, myristic, palmitic, stearic, isostearic, archidic and behenic, among the saturated fatty acids. Unsaturated fatty acids include palmitoleic, oleic, linoleic, and linolenic. Among these fatty acids, oleic is presently preferred in preparing the overbased liquid carboxylates.

The alkaline earth metal of the salt is selected from the group consisting of calcium, barium, magnesium and strontium. For example, powdered overbased calcium oleates have been prepared. These powdered overbased calcium salts contain amorphous calcium carbonate complexed with calcium oleate.

In the method of making the liquid overbased salts from which the powdered amorphous salts are derived, it is important to have an aliphatic alcohol having at least 8 carbon atoms, more preferably an alcohol having 8 to 14 carbon atoms, such as, isodecanol, dodecanol, octanol, tridecanol and tetradecanol. Isodecanol is presently preferred. It has been found that when a higher aliphatic alcohol is employed in making the liquid overbased product, phenol may be excluded from the reaction as a promoter. This is a particularly advantageous feature of the invention where it is undesirable to have a phenol or phenolic reaction product involved in the manufacture or use of the powdered overbased amorphous salts.

While not being strictly bound by theory, the liquid overbased alkaline earth salt of the fatty acid is believed to be a thermodynamically stable microemulsion. The microemulsion has micelles and a continuous phase. The micelles consist of an amorphous alkaline earth metal carbonate and an amorphous alkaline earth metal carboxylate of the fatty acid. The continuous phase of the microemulsion consists of the liquid hydrocarbon and the aliphatic alcohols or glycols which may be present. This invention is directed to isolating particles which are the agglomerated micelles of the amorphous salts to form the powdered overbased salts.

Powdered overbased amorphous metal salts have been prepared containing at least 8% by weight or more of the alkaline earth metal up to about 70% by weight. In the case of the overbased calcium salts, up to about 8% by weight calcium are produced and, for barium salts, up to about 30% by weight barium may be produced. In the preparation of higher overbased products, for example, containing about 15–70% by weight metal, it has been found suitable to use a glycol or a glycol ether along with the higher aliphatic alcohol. A glycol or glycol ether may be selected from the group consisting of diethylene glycol monobutyl ether (butyl Carbitol®), triethylene glycol, dipropylene glycol, diethylene glycol monomethyl ether, ethylene glycol monobutyl ether, and mixtures thereof.

B. The Basic Process and Critical Features of Making the Overbased Liquid and Powder Additives The process of the present invention for preparing the oil additive of a shelf stable haze free liquid of an overbased alkaline earth metal salt of a fatty acid comprises reacting an alkaline earth metal base and a fatty acid with an equivalent ratio of metal base to the fatty acid being greater than 1:1 in the presence of a mixture of liquid hydrocarbon. A surfactant and catalyst promote the reaction. The mixture is acidified and preferably carbonated to produce amorphous alkaline earth metal carbonate. During carbonation, a dispersion is added containing alkaline earth metal base, liquid hydrocarbon and an aliphatic alcohol having at least 8 carbon atoms in relative amounts at a controlled rate of base addition to produce a stable haze free liquid reaction product. Water is removed from the reaction product to produce a shelf stable haze free liquid overbased alkaline earth metal salt. Generally, it is preferred that the entire process be conducted in the absence of free oxygen and, for this purpose, an atmosphere of nitrogen is used.

As developed above, one of the important features of the method is the step of adding during carbonation a dispersion of alkaline earth metal base, liquid hydrocarbon and an aliphatic alcohol having at least 8 carbon atoms at a controlled rate of base addition to produce the stable haze free liquid. It has been found that the addition of a dispersion of the base in the liquid hydrocarbon and aliphatic alcohol protects or passivates the base, thereby enabling the formation of a stable haze free liquid reaction product. By protecting or passivating the base, carbonation proceeds to produce amorphous alkaline earth metal carbonate. Unexpectedly, the reaction proceeds without the need to remove water during the reaction and results in a very stable haze free liquid reaction product. At the end of the reaction, water is removed, preferably to the level of less than 1%, more preferably less than 0.3% or 0.1%, in the obtainment of the shelf stable liquid overbased salt. The removal of water which is added during the reaction or formed by the reaction is necessitated because it forms a separate phase which impedes either the product of the reaction or the formation of a shelf stable haze free liquid.

Other features of the method include filtering the product of the reaction to produce a shelf or thermodynamically stable liquid at a product filtration rate of at least about 300 ml per 10 minutes. In a preferred form of the invention, the product which is produced is filterable to remove unwanted byproducts and enhance the shelf stability of the overbased liquid. For example, with a Buchner funnel having a 15 cm diameter under vacuum of about 25–30 inches Hg with a Whatman No. 1 filter and a diatomaceous filtering aid (Celite® 512–577), the product is filterable at satisfactory rates. One of the important discoveries of the method of this invention is the ability to filter the reaction product to form a stable haze free liquid at filtration rates which heretofore were unachievable. This was especially the case when higher levels of metal content in the overbased liquids were desired, especially overbased calcium liquids. Thus, filtration removes undesirable impurities including silica, iron oxide and other metal species, unreacted calcium hydroxide, calcium carbonate, and other oxides which may contribute to lack of stability. These byproducts or impurities may comprise up to about 6% of byproduct of the reaction.

Throughout this specification and claims, the term "basic" or "overbased" as applied to the alkaline earth metal salts is used to refer to metal compositions wherein the ratio of total metal contained therein to the fatty acid moieties is greater than the stoichiometric ratio of the neutral metal salt. That is, the number of metal equivalents is greater than the number of equivalents of the fatty acid. In some instances, the degree to which excess metal is found in the basic metal salt is described in terms of a "metal ratio". Metal ratio as used herein indicates the ratio of total alkaline earth metal in the oil-soluble composition to the number of equivalents of the fatty acid or organic moiety. The basic metal salts often have been referred to in the art as "overbased" or "superbased" to indicate the presence of an excess of the basic component.

The process of the present invention may be used to prepare shelf stable liquids and isolated powders of the amorphous alkaline earth metal carboxylates of the fatty acids. As stated above, the method may be practiced without the use of phenol promoter or phenolic reaction product. Therefore, liquid and powdered overbased barium fatty acid carboxylates have been made without the need for a phenol or phenolic reaction product in order to achieve a shelf stable haze free liquid. In the case of liquid and powdered overbased calcium fatty acid carboxylates, shelf stable products are obtained without a phenol where the aliphatic alcohol having at least 8 carbon atoms is employed.

The alkaline earth metal bases utilized as a reaction component may be derived from any alkaline earth metals and, of these, calcium and barium bases are particularly preferred. The metal bases include metal oxides and hydroxides and, in some instances, the sulfides, hydro sulfides, etc. While a phenolic component or reactant may preferably be excluded from a reaction, in the case of liquid overbased calcium products, the phenol or alkyl phenol may be included to yield liquid overbased products. As stated above, the fatty acids, or mixtures thereof, as identified above may be used in the reaction mixture. For example, a surfactant that facilitates the reaction is the alkaline earth metal carboxylate of the fatty acid that is formed in situ. Other surfactants may be included, for example, general purpose surface active agents identified under the trademark Tween which are polyoxyethylene derivatives of fatty acid partial esters of sorbitol anhydrides, particularly mono- and di-oleates of the ethoxylated sorbitol, and polyisobutylene succinic acid. Furthermore, it is desirable to include a catalyst to facilitate the speed of the reaction such as propionic acid, citric acid, acetic acid and adipic acid. The hydrocarbon liquid employed in the process and the liquid reaction products generally includes any hydrocarbon diluent. Most generally, the liquid hydrocarbon is selected from the group of an oil, mineral spirits and non-aromatic hydrocarbons.

C. Amounts of Reactants and Catalysts

The amount of alkaline earth metal base utilized in the preparation of basic salts is an amount which is more than one equivalent of the base per equivalent of fatty acid or organic moiety, and more generally, will be an amount sufficient to provide at least three equivalents of the metal base per equivalent of the acid. Larger amounts can be utilized to form more basic compounds, and the amount of metal base included may be any amount up to that amount which is no longer effective to increase the proportion of metal in the product. When preparing the mixture, the amount of fatty acid and the alcohol included in the mixture is not critical except that the ratio of equivalents of the metal base of the combination of the other components in the mixture should be greater than 1:1 in order to provide a basic product. More generally, the ratio of equivalents will be at least 3:1. In those instances where phenol may be present in making an overbased calcium, the ratio of equivalents of monocarboxylic acid to phenol should be at least about 1.1:1; that is, the monocarboxylic acid is present in excess with respect to the phenol.

The ranges of hydrocarbon oil, aliphatic alcohol (preferably isodecanol), butyl Carbitol and triethylene glycol have been selected such that, in the presence of the alkaline earth fatty acid salt (i.e. Ca oleate) which acts as a primary surfactant, the mixture forms a stable inverse microemulsion of the metal carbonate, water, and surfactant (internal phase) and surfactant, cosurfactant, and hydrocarbon (external continuous phase).

The acceptable ratios of hydrocarbon oil to cosurfactant aliphatic alcohol (isodecanol) are about 2:1 to about 4:1, with about 2:1 preferred. The glycol ethers may be used at about 1–15% of the final product, butyl Carbitol preferably at about 6%, and triethylene glycol at about 0–2%, preferably at about 0.6%.

The lime slurry which is added to the oleic acid in the reaction is formulated to be an easily pumpable mixture with the general composition of about 40–50% lime, about 25–40% hydrocarbon oil, about 10–25% isodecanol, and about 0–10% butyl Carbitol. The butyl Carbitol amount that is needed to make a pumpable slurry increases as the % lime in the slurry increases.

The reaction mixture for an overbased calcium oleate, after addition of the slurry and carbonation with carbon dioxide, preferably has the following composition ranges:

| | |
|---|---|
| Ca oleate (surfactant) | about 15–30% |
| Ca carbonate | about 9–35% |
| Hydrocarbon oil | about 30–35% |
| Isodecanol (cosurfactant) | about 15–18% |
| Butyl Carbitol | about 4–6% |
| Triethylene glycol | about 0–0.8% |

The catalyst, propionic acid or a lower aliphatic mono, di, or tricarboxylic acid is used in the amount of about 0–0.1% of the final reaction mixture.

Substitution of magnesium, strontium, or barium for calcium in the overbased salt is done on an equivalent basis of the metal hydroxide. On the basis of the final reaction mixture, the following amounts may be used:

| | |
|---|---|
| Ca(OH)$_2$ (lime) | about 15–30% |
| Mg(OH)$_2$ | about 12–24% |
| Sr(OH)$_2$ | about 25–50% |
| Ba(OH)$_2$ | about 35–50% |

The step of carbonation involves treating the mixtures described above with an acidic gas in the absence of free oxygen until the titratable basicity is determined using phenolphthalein. Generally, the titratable basicity is reduced to a base number below about 10. The mixing and carbonation steps of the present invention require no unusual operating conditions other than preferably the exclusion of free oxygen. The base, fatty acid and liquid hydrocarbon are mixed, generally heated, and then treated with carbon dioxide as the acidic gas, and the mixture may be heated to a temperature which is sufficient to drive off some of the water contained in the mixture. The treatment of the mixture with the carbon dioxide preferably is conducted at elevated temperatures, and the range of temperatures used for this step may be any temperature above ambient temperature up to about 200° C., and more preferably from a temperature of about 75° C. to about 200° C. Higher temperatures may be used such as 250° C., but there is no apparent advantage in the use of such higher temperatures. Ordinarily, a temperature of about 80° C. to 150° C. is satisfactory.

D. Lubricating Oil Compositions

The overbased additives of this invention are complexes having a large excess of basic metal ion over that that may be neutralized by other additives in the lubricant composition. The lubricating oil composition is formulated for commercial purposes for use in internal combustion engines, especially gasoline and diesel engines, crankcase lubrication and the like. Accordingly, the overbased metal additives of this invention are endowed with an excess of basic particles which function to react with an acidic species or moiety such as carbon dioxide, or other acidic fuel combustion products which are corrosive and tend to degrade the oil and metal. The acids resulting from the fuel combustion or oil oxidation are particularly damaging to the functioning of the engine and must be neutralized. It has been found that the overbased additives of this invention are particularly advantageous in preventing such damage. Furthermore, the overbased additives of this invention provide a friction modifying function which, in the case of engine and crankcase lubrication, improves fuel economy. In addition, the overbased additives provide a detergent effect by holding solvent and other contaminants in suspension, thereby passivating them to reduce engine deposits as well as sludge. Accordingly, the advantageous properties of the metal protectant additives in the lubricant compositions of this invention will be further understood with reference to the following detailed compositions and examples.

(1) Oil Component

The oil (sometimes referred to as "base oil") is an oil of lubricating viscosity and is the primary liquid constituent of a lubricant, into which additives and possibly other oils are blended to produce the final lubricant (herein "lubricating composition").

A base oil may be selected from natural (vegetable, animal or mineral) and synthetic lubricating oils and mixtures thereof. It may range in viscosity from light distillate mineral oils to heavy lubricating oils such as gas engine oil, mineral lubricating oil, motor vehicle oil, and heavy duty diesel oil. Generally, the viscosity of the oil ranges from 2 to 30, especially 5 to 20 mm$^2$s$^{-1}$ at 100° C. Natural oils include animal oils and vegetable oils, liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and the derivatives; analogs and homologs thereof. Alkylene oxide polymers and interpolymers and derivatives thereof where the terminal hydroxyl groups have been modified, for example by esterification or etherification, constitute another class of known synthetic lubricating oils. Another suitable class of synthetic lubricating oils comprises the esters of dicarboxylic acids. Esters useful as synthetic oils also include those made from $C_5$ to $C_{12}$ monocarboxylic acids and polyols, and polyol ethers such as neopentyl glycol, trimethylolpropane, pentaerythritol, dipentaerythritol and tripentaerythritol. Silicon-based oils such as the polyalkyl-, polyaryl-, polyakoxy-, or polyaryloxysiloxane oils and silicate oils comprise another useful class of synthetic lubricants.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

(2) Co-Additives

Known additives may be incorporated into the lubricant composition together with the additives of the invention. They may, for example, include dispersants; other detergents, e.g. single or mixed detergent systems; rust inhibitors; anti-wear agents; anti-oxidants; corrosion inhibitors; friction modifiers or friction reducing agents; pour point depressants; anti-foaming agents; viscosity modifiers; and surfactants. They can be combined in proportions known in the art. As is also known in the art, some additives can provide a multiplicity of effects; thus, for example, a single additive may act as a dispersant and as an oxidation inhibitor. Certain classes of co-additives will be discussed in more detail as follows:

(a) Dispersants

A dispersant is an additive for a lubricant whose primary function is to hold solid and liquid contaminants in suspension, thereby passivating them and reducing engine deposits at the same time as reducing sludge depositions. Thus, for example, a dispersant maintains in suspension oil-insoluble substances that result from oxidation during use of the lubricant, thus preventing sludge flocculation and precipitation or deposition on metal parts of the engine. Dispersants are usually "ashless", being non-metallic organic materials that form substantially no ash on combustion, in contrast to metal-containing, and hence ash-forming, materials. They comprise a long chain hydrocarbon with a polar head, the polarity being derived from inclusion of, e.g. an O, P or N atom. The hydrocarbon is an oleophilic group that confers oil-solubility, having for example 40 to 500 carbon atoms. Thus, ashless dispersants may comprise an oil-soluble polymeric hydrocarbon backbone having functional groups that are capable of associating with particles to be dispersed. Typically, the dispersants comprise amine, alcohol, amide, or ester polar moieties attached to the polymer backbone often via a bridging group. The ashless dispersant may be, for example, selected from oil-soluble salts, esters, amino-esters, amides, imides, and oxazolines of long chain hydrocarbon-substituted mono- and dicarboxylic acids or their anhydrides; thiocarboxylate derivatives of long chain hydrocarbons; long chain aliphatic hydrocarbons having a polyamine attached directly thereto, and Mannich condensation products formed by condensing a long chain substituted phenol with formaldehyde and polyalkylene polyamine, such as described in U.S. Pat. No. 3,442,808.

Dispersants include, for example, derivatives of long chain hydrocarbon-substituted carboxylic acids, examples being derivatives of high molecular weight hydrocarbyl-substituted succinic acid. A noteworthy group of dispersants are hydrocarbon-substituted succinimides, made, for example, by reacting the above acids (or derivatives) with a nitrogen-containing compound, advantageously a polyalkylene polyamine, such as a polyethylene polyamine. Particularly preferred are the reaction products of polyalkylene polyamines with alkenyl succinic anhydrides, such as described in U.S. Pat. Nos. 3,202,678; 3,154,560; 3,172,892; 3,024,195, 3,024,237; 3,219,666; and 3,216,936; and BE-A-66,875 that may be post-treated to improve their properties, such as borated (as described in U.S. Pat. Nos. 3,087,936 and 3,254,025) fluorinated and oxylated. For example, boration may be accomplished by treating an acyl nitrogen-containing dispersant with a boron compound selected from boron oxide, boron halides, boron acids and esters of boron acids.

(b) Anti-Wear and Anti-Oxidant Agents

Dihydrocarbyl dithiophosphate metal salts are frequently used in lubricants as anti-wear and antioxidant agents. The metal may be an alkali or alkaline earth metal, or aluminum, lead, tin, zinc, molybdenum, manganese, nickel or copper. The zinc salts are most commonly used in lubricating oil in amounts of 0.1 to 10, preferably 0.2 to 2, mass %, based upon the total weight of the lubricant. They may be prepared in accordance with known techniques by first forming a dihydrocarbyl dithiophosphoric acid (DDPA), usually by reaction of one or more alcohols or a phenol with $P_2S_5$ and then neutralising the formed DDPA with a zinc compound. The zinc dihydrocarbyl dithiophosphates can be made from mixed DDPA which in turn may be made from mixed alcohols. Alternatively, multiple zinc dihydrocarbyl dithiophosphates can be made and subsequently mixed.

The following Examples illustrate additive preparation of the haze free liquid overbased salts (Examples 1–6 and 10) and the powdered overbased amorphous metal salts derived therefrom (Examples 7–9 and 11–12) in accordance with the method of the present invention. These examples are not considered to be limiting the scope of this invention. Unless otherwise indicated in the following examples and elsewhere in the specification and claims, all parts and percentages are by weight, and all temperatures are in degrees Fahrenheit.

EXAMPLE 1

10% Overbased Calcium Oleate/Carbonate

A phenol-free 10% overbased calcium oleate/carbonate was prepared according to this Example. A mixture of 308.42 g of oleic acid (1.100 moles), 213.15 g mineral oil, 154.14 g of isodecyl alcohol, 63.08 g of butyl Carbitol, 8.70 g of triethylene glycol, 26.97 g of water and 0.87 g of propionic acid was heated to 190° F., with stirring, under a nitrogen atmosphere. To the stirred mixture there was continuously added a dispersion comprised of 38.98 g mineral oil, 13.86 g isodecyl alcohol, 3.71 g butyl Carbitol and 43.28 g of lime (0.5498 moles) for about 33 minutes to produce a solution of calcium oleate in the mixture. The dispersion was added at a rate of about 3 g per minute. At this point in the reaction, the mixture tested basic with phenolphthalein (about 10–12 pH). Then, to the stirred mixture there was continuously added, over a period of about 3 hours and 56 minutes, a dispersion comprised of 276.25 g mineral oil, 98.23 g isodecyl alcohol, 26.31 g butyl Carbitol and 306.75 g lime (3.897 moles) while the mixture was being treated with carbon dioxide at 1.5 SCFH at 195–200° F. The dispersion was also added at a rate of about 3 g per minute. The basicity of the reaction was checked to maintain the basicity during the reaction. When the reaction mixture tested nearly neutral to phenolphthalein, the carbon dioxide addition was discontinued. The reaction mixture was then heated to 300° F. and a total of 99.36 g of water was removed via a Dean-Stark trap. The resulting product mixture was stirred and 24.00 g of filter aid (diatomaceous earth) was added. The product mixture was filtered with suction, as stated above in the description, at about 300 ml per 10 minutes, yielding a clear, amber, mobile liquid filtrate of overbased calcium oleate/carbonate which remained clear upon cooling to room temperature. The filtrate was analyzed to contain 10.4% Calcium by weight.

EXAMPLE 2

14% Overbased Calcium Oleate/Carbonate

A phenol-free overbased calcium oleate/carbonate containing 14% calcium by weight was made according to this Example. In a 3-liter resin kettle equipped with an overhead stirrer, two gas inlet tubes, a thermocouple, heating mantle and Dean-Stark trap with condenser, was added 1700 g of a 9.89% overbased calcium oleate/carboxylate made by the method of the previous example and 42.5 g of deionized water. The mixture was heated with stirring under a nitrogen atmosphere to a temperature of 195° F., and a slurry containing 385 g of hydrated lime (94% calcium hydroxide), 231 g of hydrocarbon oil, 96.25 g of isodecyl alcohol, and 57.75 g of butyl Carbitol was added at a rate of 3.42 g per minute over a 3 hour 45 minute period. After 5 minutes of slurry addition, carbon dioxide was added to the reaction at a rate of 1.2 standard cubic feet per hour. During the carbonation, a temperature of 195–200° F. was maintained and pH was monitored as in Example 1.

After the slurry addition was finished, the carbon dioxide addition was continued until the reaction mixture was neutral, as shown by a colorless sample when tested with phenolphthalein. The reaction mixture was then heated to 300° F. and both the water added and the water produced in the reaction was removed via the Dean-Stark trap. To the dehydrated reaction product was added 75 g of diatomaceous earth and the product was filtered with suction, as above in Example 1, yielding a clear, amber, mobile liquid filtrate of overbased calcium oleate/carboxylate which remained clear on cooling to room temperature. The filtrate was analyzed to contain 14.5% calcium by weight.

EXAMPLE 3

10% Overbased Calcium Oleate/Carbonate, GRAS Indirect Food Additive Formula

A phenol-free 10% overbased calcium oleate/carbonate containing only materials generally recognized as safe as indirect food additive was prepared as follows. A mixture of 520.6 g of oleic acid (1.85 moles), 522 g of Shellflex™ 6111 light mineral oil, 259 g of dodecyl alcohol, and 32.4 g of propylene glycol was heated to 180° F. and 2.0 g of propionic acid and 15.0 g of water was added. To the stirred reaction mixture there was continuously added a slurry comprised of 345.6 g of Shellflex™ 6111, 172.8 g of dodecyl alcohol, 21.6 g of propylene glycol, and 540 g of lime (94% available as calcium hydroxide) at a rate of 4.0 g per minute. After approximately 41 minutes of slurry addition, the oleic acid was neutralized and excess lime was present and partially dissolved to give an apparent pH of 11.4. Then carbon dioxide gas was passed into the reaction mixture through a subsurface addition tube at a rate of approximately 495 ml/minute to produce and maintain a pH of 10.5–11 for the duration of the slurry addition (approximately 5.25 hours), while maintaining the reaction temperature at 190–192° F. with mild cooling. When approximately 1080 g of slurry had been added, the slurry addition was turned off and the carbon dioxide addition was continued until the pH of the reaction dropped to 7.5 (approximately 7 minutes). The reaction was carefully placed under 22.5 inches of vacuum and heated to 310° F. over a 1.75-hour period while removing the added water and the water of reaction via a Dean-Stark tube. The reaction was held at 310° F. and 30 g of diatomaceous earth filter aid was added. The product was filtered hot with suction as stated in the previous example at a rate of 545 ml per 10 minutes, yielding a clear, yellow-amber mobile filtrate of overbased calcium oleate/carbonate which remained clear on cooling to room temperature. The filtrate was analyzed to contain 10.5% calcium by weight. The infrared spectrum of the material showed a peak at 864 reciprocal centimeters, characteristic of amorphous calcium carbonate.[1]

[1] The physical state of the calcium carbonate in the materials prepared in the examples was analyzed by X-ray powder pattern for crystallinity and by infrared spectra. Amorphous calcium carbonate has an infrared absorption at 864 reciprocal centimeters, according to a paper "Infrared Spectra of Amorphous and Crystlline Calcium Carbonate" by Andersen and Brecevic, Acta Chemica Scandinavica 45 (1991) 1018–1024. The other crystalline polymorphs of calcium carbonate, calcite, aragonite and vaterite have corresponding infrared absorptions at 877, 856, and 877 reciprocal centimeters, respectively.

EXAMPLE 4

15% Overbased Calcium Oleate/Carbonate

A highly overbased calcium oleate/carbonate containing 15.4% calcium by weight was produced by the following procedure. To a mixture of 1700 g of an 11.4% overbased calcium oleate/carbonate liquid produced according to the previous example was added 50 g of water and the mixture was heated to 190° F. under stirring at 1000 rpm. To the mixture was added a 720 g portion of a slurry made from 500 g of lime (94% available as calcium hydroxide), 320 g of Shellflex™ 6111 light mineral oil, 160 g of dodecyl alcohol, and 20 g of propylene glycol at a rate of 3.97 g per minute over a 3 hour 40 minute period. After 2 minutes of slurry addition, carbon dioxide gas was introduced to the reaction mixture through a subsurface addition tube at a rate to produce and maintain the apparent pH of the reaction mixture at a value of 10.5–11 (approximately 450–550 ml/minute). After the time required to add the required amount of lime slurry passed, the slurry addition was discontinued and the carbon dioxide addition continued until the pH of the reaction fell to 7.5 (about 10 minutes). The reaction was then heated under a vacuum of 22.5" while heating slowly to 310° F. The water added and the water of reaction was removed via a Dean-Stark trap. The reaction mixture was then filtered through a bed of diatomaceous earth (filter aid) to give a clear, amber mobile filtrate of a highly overbased calcium oleate/carbonate. The material was analyzed to contain 15.4% calcium by weight. The infrared spectrum of the material showed a characteristic peak for amorphous calcium carbonate at 864 reciprocal centimeters.

EXAMPLE 5

14% Overbased Strontium Oleate/Carbonate

A phenol-free strontium oleate/carbonate containing about 14% strontium was prepared by the following procedure. A mixture of 413 g of oleic acid, 600 g of Shellflex™ 6111 light mineral oil, 300 g of isodecyl alcohol, 40 g of butyl carbitol, and 4 g of triethylene glycol was heated to 176° F., and 1000 g of strontium hydroxide octahydrate was added. The reaction mixture was heated to 275° F. over a 2.5-hour period, while removing 550 g of water via a Dean-Stark trap with the aid of a nitrogen sparge at 2.0 SCFH. After the rate of water removal slowed, the nitrogen sparge was turned off, and carbon dioxide gas was added to the reaction via a subsurface addition tube at a rate of 450 ml/minute, and the water formed was continually removed. After 7 hours of carbon dioxide addition at 250–275° F., the carbon dioxide was turned off, the temperature of the reaction was raised to 300®F. and the remaining water was removed with the assistance of a nitrogen sparge at 2.0 SCFH. The reaction was then filtered hot with suction with the assistance of filter aid, yielding the overbased strontium oleate carbonate as a light yellow, clear mobile liquid. The product was analyzed to contain 14.25% strontium by weight.

EXAMPLE 6

4.5% Overbased Magnesium Oleate/Carbonate

A phenol-free magnesium oleate/carbonate containing about 4.5% magnesium was prepared by the following procedure. A mixture of 529.3 g of oleic acid, 600 g of Shellflex™ 6111 light mineral oil, 400 g of isopropyl alcohol, 350 g of isodecyl alcohol, 400 g of water was heated to 140° F. and 400 g of magnesium hydroxide was added. The neutralization of the acid with the magnesium hydroxide caused the temperature to rise to 167° F. Carbon dioxide gas was passed into the reaction mixture through a subsurface addition tube at a rate of 225 ml/minute for 6 hours, during which time the temperature was gradually raised to 223° F. and 720 ml of a mixture of water and isopropyl alcohol was removed. The temperature was raised to 305° F. and the remaining water was removed with the assistance of the carbon dioxide addition. The carbon dioxide addition was stopped, and the hot reaction mixture was filtered with suction with the assistance of filter aid, giving the overbased magnesium product as a clear light yellow mobile liquid. The product was analyzed to contain 4.5% magnesium by weight.

EXAMPLE 7

21.38% Overbased Amorphous Calcium Oleate/Carbonate Powder

To 1000 g of rapidly stirred isopropyl alcohol was added 200 g of an overbased calcium oleate/carbonate liquid containing 10.5% calcium by weight (product prepared as in Example 3) in a steady stream over a period of 5 minutes. The mixture was stirred at room temperature for 1 hour, and then filtered with suction. The filter cake was washed with 2×100 g of isopropyl alcohol, sucked as dry as possible, and then allowed to dry at room temperature overnight. The powder obtained showed no crystalline nature by x-ray powder pattern, and dispersed easily in mineral oil to give a clear, isotropic, non-viscous dispersion. The powder was found to contain 21.38% calcium by weight. An infrared spectrum of the powder (nujol mull) showed a peak at 866 reciprocal centimeters, characteristic of amorphous calcium carbonate.

EXAMPLE 8

20.2% Overbased Amorphous Calcium Oleate/Carbonate Powder

A powdered overbased amorphous calcium oleate/carbonate was prepared according to the following example. To 1500 g of isopropyl alcohol, rapidly stirred and heated to reflux, 500 g of overbased calcium oleate/carbonate liquid containing 9.76% calcium by weight (product of example 1 above) was added over a 15-minute period. The mixture was allowed to reflux a further ½ hour, and then allowed to cool to 90° F. and filtered with suction. The collected solids were washed with 2×125 g of isopropyl alcohol, and sucked as dry as possible. The solid product was allowed to dry at room temperature overnight and yielded 262 g of an off-white solid, which was analyzed to contain 20.2% calcium by weight. Tne miaterial was easily dispersed in minprql oil at 70% solid to give a clear, mobile dispersion with a calcium content of 13.83% by weight. An infrared spectrum of the powder (nujol mull) showed a peak at 866 reciprocal centimeters, characteristic of amorphous calcium carbonate. The powder particles, dispersed in mineral spirits, showed a mean particle diameter of 0.112 microns.

EXAMPLE 9

28% Overbased Amorphous Calcium Oleate/Carbonate Powder

A powdered overbased amorphous calcium oleate/carbonate powder was prepared according to the following example. 200 g of an overbased calcium oleate/carbonate liquid dispersion containing 15.4% calcium by weight (prepared by Example 4, above) was added in a steady stream to 1000 g of rapidly stirred isopropyl alcohol in a 5-minute period. The mixture was stirred at room temperature for an additional hour, then filtered with suction, washed with 2×100 ml of isopropyl alcohol, and sucked as dry as possible. The product was allowed to dry in air at room temperature overnight, yielding a free-flowing off-white powder that was analyzed to contain 28% calcium by weight. An infrared spectrum of the powder (nujol mull) showed a peak at 866 reciprocal centimeters, characteristic of amorphous calcium carbonate. An X-ray powder pattern showed only broad peaks, with no peaks from calcite (crystalline calcium carbonate). The powder, dispersed in mineral spirits, showed a mean particle diameter of 0.0566 microns.

EXAMPLE 10

30% Overbased Amorphous Barium Oleate/Carbonate

A phenol-free overbased amorphous barium oleate/carbonate was prepared according to the following example. A mixture of 502.5 g of oleic acid, 581 g of HVI mineral oil, 200.0 g of Epal™ 14–18 (a mixture of aliphatic alcohols containing 14 to 18 carbon atoms), 102 g of butyl carbitol (diethylene glycol monobutylether and 10.2 g or triethylene glycol was heated to 178° F. under a slow stream of nitrogen. To the heater reaction mixture was added 1034.1 g of barium hydroxide monohydrate in three increments over a 45-minute period. The temperature of the reaction mixture was then raised to 280° F. over a one-hour period, and 75.6 g of water was removed via a Dean-Stark trap with the aid of the nitrogen flow of 2 SCFH. The nitrogen flow was reduced to 1 SCFH and carbon dioxide was added via a subsurface addition tube at a rate of about 300 ml/min over a 5½ hour period, during which time the temperature was gradually raised from 280° F. to 300° F. and water was removed via a Dean-Stark trap at the approximate rate of 7.5 g every 15 minutes after 2 hours.

At the end of the carbon dioxide addition time, the reaction was carefully placed under 22 inches of vacuum and the remaining water was removed, along with a small amount of butyl carbitol. The total water removed was 210 g. After 30 g minutes, the vacuum was released, and 40 g of filter aid (diatomaceous earth) was added. The mineral was filtered by suction to give a clear, amber, mobile liquid which was analyzed to contain 29.7% barium by weight.

EXAMPLE 11

45.2% Overbased Amorphous Barium Oleate/Carbonate Powder

A phenol-free overbased barium oleate/carbonate containing 29.7% barium by weight (prepared by Example 10) was poured in a slow stream in 5 minutes into 1000 g of isopropyl alcohol under rapid stirring. The mixture was allowed to stir at room temperature for 1 hour, and then filtered with suction, washed with 2×100 g of isopropyl alcohol, sucked as dry as possible then allowed to dry in air overnight. The product, an off-white powder, as analyzed to contain 45.2% barium by weight.

EXAMPLE 12

45.5% Overbased Amorphous Barium Oleate/Phenate/Carbonate Powder

A phenol-containing overbased amorphous barium oleate/phenate/carbonate liquid containing 45.5% barium was prepared according to Example 10 with the addition of phenol to the reaction mixture, as, for example, disclosed in U.S. Pat. No. 5,830,935. 200 g of this overbased barium oleate/phenate/carbonate was added to 1000 g of rapidly stirred isopropyl alcohol at room temperature over a 5-minute period. The mixture was allowed to stir for 1½ hours, then was filtered with suction, washed 2×100 g of isopropyl alcohol, sucked as dry as possible, and allowed to dry in air. The product, a pink powder, was analyzed to contain 45.5% barium by weight.

Lubricant Composition Formulation and Evaluation

In order to demonstrate the advantageous properties of the lubricant compositions of this invention which contain the metal protectant overbased additive, a number of formulations were made and evaluated. In the preparation of the lubricant compositions, it is conventional practice to introduce the additives in the form of concentrate in a suitable carrier, for example, lubricating oil or other suitable solvent. Aliphatic, naphthenic and aromatic hydrocarbons are examples of suitable carrier fluids for the additive concentrates. The concentrates formulated hereinafter have been designated under the term "DI Package". The final package includes the formulation of the DI Package with the base oil or other viscosity improver. Accordingly, in TABLE 1, the liquid overbased calcium oleate/carbonate of EXAMPLE 1 above is used as the metal protectant additive of this invention as formulated in the Package Sample B of TABLE 1 and included in the final lubricant composition by adding the additives of the Package to the lubricating oil as set forth in TABLE 1. The level of the overbased calcium oleate/carbonate in the final lubricant composition is about 0.7% by weight to the composition.

With reference to TABLE 1, the overbased calcium oleate/carbonate (OBCO) additive of this invention in Sample B was compared to an overbased calcium sulfonate (OBCS) additive of a regular oil (Sample A). In the case of Sample B, the OBCO was evaluated for detergency in the presence of a friction modifier. Also, the OBCO was evaluated for lubricity without the friction modifier in Sample C. In the case of Sample D, no OBCO, no OBCS and no friction modifier were employed, as a negative control. Panel Coker Testing was employed to determine the detergency of Samples A–D of TABLE 1. The Panel Coker Test is a quick laboratory method that can determine the relative deposit-forming tendency of the lubricant. This is achieved by splashing lubricant against a heated metal plate. The Panel Coker Test isolates the engine cleanliness variables of high temperature stability and surface activity to prevent deposition of any oxidized material from the bulk oil. The UEC Panel Coker Test results are shown in TABLE 2 by measuring the weight of deposits which are caused by thermal and oxidated stresses due to lubricant degradation under the test conditions at an elevated temperature of 600° F., 330 ml of sample for 6 hours.

TABLE 1

| | | | | | |
|---|---|---|---|---|---|
| Final Batch size (grams): | | 1750.0 | 1750.0 | 1750.0 | 1750.0 | 1750.0 |
| Final Batch Volume (ml): | | 2046.8 | 2046.8 | 2046.8 | 2046.8 | 2046.8 |

| Purpose of Blend: Component | Percent of Blend | Regular Oil Positive Control | Evaluate Detergency + OBCO + FM | Evaluate Lubricity – FM + OBCO | No FM or Detergent Negative Control |
|---|---|---|---|---|---|
| DI Package: | | A | B | C | D |
| H-646 (Dispersant) | 5.00 | 87.50 | 87.50 | 87.50 | 87.50 |
| OBCO (Overbased Calcium Oleate) | 1.50 | — | 24.50 | 24.50 | — |
| H-611 (Overbased Calcium Sulfonate) | 1.40 | 24.50 | — | — | — |
| H-614 (Neutral Sulfonate Detergent) | 0.75 | 13.13 | 13.13 | 13.13 | 13.13 |
| H-7169 (Anti-Wear) | 1.00 | 17.50 | 17.50 | 17.50 | 17.50 |
| K-2000 (Friction Modifier) | 1.75 | 30.63 | 30.63 | — | — |
| N-438L (Anti-Oxidant) | 0.75 | 13.13 | 13.13 | 13.13 | 13.13 |
| Star 4 Oil (Group II Base Oil) | 0.40 | 7.0 | 7.0 | 37.63 | 62.13 |
| Antifoam A (Defoamer) | 10 ppm | 0.0175 | 0.0175 | 0.0175 | 0.0175 |
| Final Package: | | | | | |
| Star 4 Oil (Group II Base Oil) | 79.95 | 1399.13 | 1399.13 | 1399.13 | 1399.13 |
| DI Package | 11.05 | 193.38 | 193.38 | 193.38 | 193.38 |
| Viscoplex (VI Improver) | 9.0 | 157.50 | 157.50 | 157.50 | 157.50 |
| Total Weight: | | 1750.00 | 1750.00 | 1750.00 | 1750.00 |
| Wt. of Star 4 needed: | | 1406.13 | 1406.13 | 1436.75 | 1461.25 |

With respect to the above Table 1, the following is a further identification of the components:

| | | | |
|---|---|---|---|
| H-611 (Overbased Calcium Sulfonate) | HiTec-611* | OB Calcium Sulfonate | Ethyl |
| H-614 (Neutral Calcium Sulfonate) | HiTec-614* | Neutral Ca Sulfonate | Ethyl |
| H-7169 (Anti-Wear) | HiTec-7169* | Zinc Dialkyl Dithiophosphate | Ethyl |
| K-2000 (Friction Modifier) | Kemester 2000 | Glycerol Monooleate | Crompton |
| N-438L (Anti-oxidant) | N-438L | Nonylated diphenylamine | Crompton |
| Star 4 Oil (Group II Base Oil) | Star 4 Oil | Hydrotreated Parrafinic Mineral Oil | Motiva |
| Anti-Foam A (Defoamer) | Antifoam "A" | Octamethylcyclotetrasiloxane | Dow |
| Viscoplex (VI Improver) | Viscoplex 6-917 | Acrylic Polymer/Neutral Oils | Degussa |

*The additives has mineral oil and petroleum distillates as diluents

TABLE 2

Panel Coker Test Results - mg Deposit

| Blends | Test 1 | Test 2 | Average | Notes |
|---|---|---|---|---|
| A | 205 | 235 | 220 | OBCS |
| B | 133 | 124 | 128 | OBCO |
| C | 167 | 189 | 178 | OBCO/No FM |
| D | 289 | 252 | 270 | No OBCO/No FM |

Test Conditions: 600° F., 330 ml of sample, 6 hours

With reference to TABLE 2, the formulations of TABLE 1 were tested and the following observations were made. Good results are shown for the lubricant compositions containing the inventive OBCO metal protectant with an average test result for Samples B and C of 128 and 178 mg of deposit, respectively. In contrast, the regular oil which contain the OBCS produced an average of 220 mg of deposit (Sample A) and 270 mg in the case of Sample D. Accordingly, the OBCO of this invention demonstrated superior detergency in comparison to a typical regular oil having an OBCS and other compositions which contain no overbased or friction modifier additives.

The oxidation stability or stability of the lubricating composition of this invention to resist the corrosiveness or acid moieties resulting from fuel combustion or oil oxidation were tested. The analysis of oxidation characteristics of the lubricant compositions were tested according to ASTM D943. This procedure is used to evaluate the oxidation stability of Samples A–D in the presence of oxygen, water, and iron and copper metals at a high temperature (95° C.). The ASTM D943 test is a low temperature oxidation-corrosion test for lubricants such as steam turbine oils and hydraulic fluids expected to encounter wet conditions, yet be expected to last a very long time. Thus, the D943 test conditions are run at 95° C. in the presence of liquid water in contact with copper and iron metal catalyst coupons with pure oxygen gas bubbling through the mixture as the oxidizing agent. Success in the ASTM D943 test requires that the lubricant formulation offer a good deal of protection to the iron and copper metal, as well as having a base reserve which will last long enough to reach the 1000 hour minimum time for this base reserve to be depleted and the oil to reach an acid number of 2. The results of the testing for the OBCO of the additive of this invention in comparison to the OBCS as formulated in TABLE 1 are shown in TABLE 3.

TABLE 3

Acid Number, ASTM D 3339

| Time, hours | OBCS Sample A Of TABLE 1 | OBCO Sample B Of TABLE 1 |
|---|---|---|
| 0 | 2.13 | 1.93 |
| 500 | 0.58 | — |
| 668 | 0.66 | 1.26 |
| 836 | 0.69 | 1.43 |
| 1000 | — | 1.59 |
| 1004 | 0.74 | — |
| 1172 | 1.26 | — |
| 1196 | 1.40 | — |
| 1340 | — | 1.56 |
| 1508 | 1.67 | 1.57 |
| 1676 | 2.58 | 1.72 |
| 1844 | — | 1.70 |
| 2012 | — | 1.96 |
| 2180 | — | 1.98 |
| 2348 | — | 1.64 |
| 2516 | — | 1.36 |
| 2852 | — | 1.73 |
| 3020 | — | 1.84 |
| 3500 | — | 2.14 |

With reference to TABLE 3, the OBCO metal protectant additive in the lubricating composition of this invention demonstrated superior performance over the OBCS as an alkalinity source in a low temperature oxidation application. More specifically, the TABLE 3 demonstrates that it takes almost triple the time to reach an acid number (TAN) of 2.0 for the OBCO oleate additive of this invention by comparison to the OBCS sulfonate aditive. In the case of the OBCS, the acid number of 2.58 was reached after 1676 hours of testing whereas the acid number for the OBCO of 2.14 was reached after 3500 hours of testing. It has been hypothesized that the higher TAN value early in the test for the OBCO sample is evidence of a buffering action that may be formed by the oleate in contrast to the sulfonate. Thus, in the early part of the test, the 1.2 TAN value for the oleate is almost double that of the sulfonate. However, the long term performance of the OBCO oleate far exceeds the long term performance of the OBCS sulfonate. Wherefore, the lubricant compositions of this invention containing a unique OBCO additive far exceed the performance of the currently existing regular oil composition from the standpoint of resistance to damaging acids which otherwise affect the proper functioning of the engine and degrade the lubricant.

The OBCS and OBCO Samples A and B of TABLE 1 were also tested along with a Sample E which was an overbased calcium isostearate/carbonate made in accordance with the method of this invention by substituting isostearic acid for the oleic acid in Example 1 above. Upon testing the OBCS, OBCO and OBIS (overbased isostearate/carbonate) samples for their friction modifying characteristics according to ASTM D-5706 and D-5707, the inventive additives of this invention exceeded the performance of the OBCS sample. More specifically, according to ASTM D-5706, the OBCO and OBIS additives of this invention out-performed the OBCS samples by carrying a higher load for a longer period of time. In the case of the ASTM D-5707 friction and wear test, again, the inventive OBCO and OBIS additives out-performed the OBCS additive.

The above description provides a disclosure of particular embodiments of the invention and is not intended for the purpose of limiting the same thereto. As such, the invention is not limited to only the above described embodiments, rather, it is recognized that one skilled in the art would understand alternative embodiments in view of the above description that fall within the scope of the invention.

What is claimed is:

1. A lubricating oil composition comprising a lubricating oil and as a metal protectant, an additive selected from the group consisting of
   (a) a shelf stable haze free liquid of an overbased amorphous alkaline earth metal carbonate of a fatty acid and
   (b) a powdered overbased amorphous alkaline earth metal carbonate of a fatty acid isolated from said liquid, said liquid or powdered additive prepared according to the process of (i) reacting an alkaline earth metal base and a fatty acid with an equivalent ratio of metal base to fatty acid being greater than 1:1 in the presence of liquid hydrocarbon, (ii) carbonating the mixture to produce amorphous alkaline earth metal carbonate, (iii) adding during carbonation a dispersion of alkaline earth meta base, a liquid hydrocarbon and an aliphatic alcohol having at least 8 carbon atoms in relative amounts at a controlled rate of alkaline earth metal base addition to produce a stable haze free liquid reaction product, and (iv) removing water from the reaction product to obtain said liquid additive or powdered additive.

2. The lubricating oil composition of claim 1 wherein said liquid reaction product is filtered to produce a thermodynamically stable liquid at a product filtration rate of at least about 300 ml per 10 minutes.

3. The lubricating oil composition of claim 1 wherein said fatty acid is a $C_{12}$–$C_{22}$ fatty acid.

4. The lubricating oil composition of claim 1 wherein said fatty acid is oleic acid or isostearic acid.

5. The lubricating oil composition of claim 1 wherein water is removed to provide a microemulsion product having less than about 1% by weight water of the total product.

6. The lubricating oil composition of claim 1 wherein said alkaline earth metal is selected from the group consisting of calcium, barium, magnesium and strontium.

7. The lubricating oil composition of claim 1 wherein said alkaline earth metal is calcium.

8. The lubricating oil composition of claim 1 wherein the overbased salt is calcium oleate/carbonate.

9. The lubricating oil composition of claim 1 wherein the overbased salt is essentially free of a phenol or phenolic derivative.

10. The lubricating oil composition of claim 1 wherein said aliphatic alcohol has 8 to 14 carbon atoms.

11. The lubricating oil composition of claim 10 wherein the alcohol is isodecanol.

12. The lubricating oil composition of claim 11 wherein the dispersion further contains a glycol or a glycol ether.

13. The lubricating oil composition of claim 12 wherein the glycol or glycol ether is selected from the group consisting of diethylene glycol monobutyl ether, triethylene glycol, dipropylene glycol, diethylene glycol monomethyl ether, ethylene glycol monobutyl ether, and mixtures thereof.

14. The lubricating oil composition of claim 1 wherein said reaction product is formed by reacting on the basis of the final reaction mixture an amount of an alkaline earth metal base selected from the group consisting of about 15–30% calcium hydroxide, about 12–24% magnesium hydroxide, about 25–50% strontium hydroxide, and about 35–50% barium hydroxide, and mixtures thereof.

15. The lubricating oil composition of claim 14 wherein the alkaline earth metal base is calcium hydroxide and the fatty acid is oleic acid.

16. The lubricating oil composition of claim 15 wherein the haze free liquid calcium oleate is a microemulsion having amorphous calcium carbonate within the micelles of the microemulsion.

17. The lubricating oil composition of claim 1 wherein after the addition of the dispersion and carbonation with carbon dioxide the mixture contains about 15–30% calcium oleate,
about 9–35% calcium carbonate,
about 30–35% hydrocarbon oil,
about 15–18% isodecanol, and
about 4–6% glycol or glycol ether.

18. The lubricating oil composition of claim 17 wherein the dispersion contains about 40–50% calcium hydroxide, about 25–40% hydrocarbon oil, about 10–25% isodecanol and about 0–10% glycol or glycol ether.

19. The lubricating oil composition of claim 1 wherein the additive is in an amount to provide about 0.5 to about 15% by weight of the overbased metal carbonate based on the total weight of the oil composition.

20. The lubricating oil composition of claim 1 wherein the additive is in an amount to provide about 0.5 to about 7% by weight of the overbased metal carbonate based on the total weight of the oil composition.

21. The lubricating oil composition of claim 1 wherein the additive is in an effective amount to protect metal during its lubrication with said composition by neutralization of acid moieties.

22. The lubricating oil composition of claim 1 wherein the additive is in an effective amount to protect metal during its lubrication with said composition by improving detergency.

23. The lubricating oil composition of claim 1 wherein the additive is in an effective amount to protect metal during its lubrication with said composition by improving anti-wear properties.

24. A lubricating oil composition comprising a lubricating oil and, as a metal protectant, an additive of a powdered overbased amorphous alkaline earth metal carbonate of a fatty acid consisting essentially of isolated solid agglomerated micelles of a complexed salt of an amorphous alkaline earth metal carbonate complexed with an amorphous alkaline earth metal carboxylate of a fatty acid.

25. The lubricating oil composition of claim 24 wherein said fatty acid is a $C_{12}$–$C_{22}$ fatty acid.

26. The lubricating oil composition of claim 24 wherein said fatty acid is oleic acid or isostearic acid.

27. The lubricating oil composition of claim 24 wherein water is removed to provide a microemulsion product having less than about 1% by weight water of the total product.

28. The lubricating oil composition of claim 24 wherein said alkaline earth metal is selected from the group consisting of calcium, barium, magnesium and strontium.

29. The lubricating oil composition of claim 24 wherein said alkaline earth metal is calcium.

30. The lubricating oil composition of claim 24 wherein the overbased salt is calcium oleate/carbonate.

31. The lubricating oil composition of claim 24 wherein the additive is in an amount to provide about 0.5 to about 15% by weight of the overbased metal carbonate based on the total weight of the oil composition.

32. The lubricating oil composition of claim 24 wherein the additive is in an amount to provide about 0.5 to about 7% by weight of the overbased metal carbonate based on the total weight of the oil composition.

33. The lubricating oil composition of claim 24 wherein the additive is in an effective amount to protect metal during its lubrication with said composition by neutralization of acid moieties.

34. The lubricating oil composition of claim 24 wherein the additive is in an effective amount to protect metal during its lubrication with said composition by improving detergency.

35. The lubricating oil composition of claim 24 wherein the additive is in an effective amount to protect metal during its lubrication with said composition by improving anti-wear properties.

36. The lubricating oil composition of claim 1 wherein the lubricating oil is a synthetic lubricating oil.

37. The lubricating oil composition of claim 36 wherein the synthetic lubricating oil is a hydrocarbon oil.

38. The lubricating oil composition of claim 37 wherein the hydrocarbon oil is selected from the group consisting of polymerized olefins and interpolymerized olefins.

39. The lubricating oil composition of claim 36 wherein the synthetic lubricating oil is an ester.

40. The lubricating oil composition of claim 39 wherein the ester is a carboxylic acid ester made from (a) a monocarboxylic acid or a dicarboxylic acid and (b) a polyol or a polyol ether.

41. The lubricating oil composition of claim 1 wherein the lubricating oil is a natural lubricating oil.

42. The lubricating oil composition of claim 41 wherein the natural lubricating oil is selected from the group consisting of animal oils, vegetable oils, liquid petroleum oils, hydrorefined mineral lubricating oils of paraffinic types, hydrorefined mineral lubricating oils of naphthenic types, hydrorefined mineral lubricating oils of mixed paraffinic-naphthenic types, solvent-treated mineral lubricating oils of paraffinic types, solvent-treated mineral lubricating oils of naphthenic types, solvent-treated mineral lubricating oils of mixed paraffinic-naphthenic types, acid-treated mineral lubricating oils of paraffinic types, acid-treated mineral lubricating oils of naphthenic types, and acid-treated mineral lubricating oils of mixed paraffinic-naphthenic types.

43. The lubricating oil composition of claim 1 wherein the lubricating oil is selected from the group consisting of a synthetic lubricating oil and a natural lubricating oil, and mixtures thereof, and the overbased salt is a calcium oleate/carbonate.

44. The lubricating oil composition of claim 43 wherein the overbased salt is essentially free of a phenol or phenolic derivative.

45. The lubricating oil composition of claim 43 wherein the synthetic lubricating oil is a hydrocarbon oil.

46. The lubricating oil composition of claim 43 wherein the natural lubricating oil is selected from the group consisting of animal oils, vegetable oils, liquid petroleum oils, hydrorefined mineral lubricating oils of paraffinic types, hydrorefined mineral lubricating oils of naphthenic types, hydrorefined mineral lubricating oils of mixed paraffinic-naphthenic types, solvent-treated mineral lubricating oils of paraffinic types, solvent-treated mineral lubricating oils of naphthenic types, solvent-treated mineral lubricating oils of mixed paraffinic-naphthenic types, acid-treated mineral lubricating oils of paraffinic types, acid-treated mineral lubricating oils of naphthenic types, and acid-treated mineral lubricating oils of mixed paraffinic-naphthenic types.

47. The lubricating oil composition of claim 24 wherein the lubricating oil is a synthetic lubricating oil.

48. The lubricating oil composition of claim 47 wherein the synthetic lubricating oil is a hydrocarbon oil.

49. The lubricating oil composition of claim 48 wherein the hydrocarbon oil is selected from the group consisting of polymerized olefins and interpolymerized olefins.

50. The lubricating oil composition of claim 47 wherein the synthetic lubricating oil is an ester.

51. The lubricating oil composition of claim 50 wherein the synthetic lubricating oil is a carboxylic acid ester made from (a) a monocarboxylic acid or a dicarboxylic acid and (b) a polyol or a polyol ether.

52. The lubricating oil composition of claim 24 wherein the lubricating oil is a natural lubricating oil.

53. The lubricating oil composition of claim 52 wherein the natural lubricating oil is selected from the group consisting of animal oils, vegetable oils, liquid petroleum oils, hydrorefined mineral lubricating oils of paraffinic types, hydrorefined mineral lubricating oils of naphthenic types, hydrorefined mineral lubricating oils of mixed paraffinic-naphthenic types, solvent-treated mineral lubricating oils of paraffinic types, solvent-treated mineral lubricating oils of naphthenic types, solvent-treated mineral lubricating oils of mixed paraffinic-naphthenic types, acid-treated mineral lubricating oils of paraffinic types, acid-treated mineral lubricating oils of naphthenic types, and acid-treated mineral lubricating oils of mixed paraffinic-naphthenic types.

54. The lubricating oil composition of claim 24 wherein the lubricating oil is selected from the group consisting of a synthetic lubricating oil and a natural lubricating oil, and mixtures thereof, and the overbased salt is a calcium oleate/carbonate.

55. The lubricating oil composition of claim 54 wherein the overbased salt is essentially free of a phenol or phenolic derivative.

56. The lubricating oil composition of claim 54 wherein the synthetic lubricating oil is a hydrocarbon oil.

57. The lubricating oil composition of claim 54 wherein the natural lubricating oil is selected from the group consisting of animal oils, vegetable oils, liquid petroleum oils, hydrorefined mineral lubricating oils of paraffinic types, hydrorefined mineral lubricating oils of naphthenic types, hydrorefined mineral lubricating oils of mixed paraffinic-naphthenic types, solvent-treated mineral lubricating oils of paraffinic types, solvent-treated mineral lubricating oils of naphthenic types, solvent-treated mineral lubricating oils of mixed paraffinic-naphthenic types, acid-treated mineral lubricating oils of paraffinic types, acid-treated mineral lubricating oils of naphthenic types, and acid-treated mineral lubricating oils of mixed paraffinic-naphthenic types.

58. The lubricating oil composition of claims 37, 40, 42, 43, 46, 48, 51, 53, 54, or 57 and wherein the additive is in an amount to provide about 0.5 to about 15% by weight of the overbased metal carbonate based on the total weight of the oil composition.

59. The lubricating oil composition of claim 58 wherein the additive is present in an amount to provide about 0.5 to about 7% by weight of the overbased metal carbonate based on the total weight of the oil composition.

* * * * *